United States Patent [19]
Magidson et al.

[11] Patent Number: 5,957,136
[45] Date of Patent: Sep. 28, 1999

[54] EARPLUG

[75] Inventors: Mark Magidson, Los Angeles; Dan Dix, Irvine, both of Calif.

[73] Assignee: Moldex-Metric, Inc., Culver City, Calif.

[21] Appl. No.: 09/169,742

[22] Filed: Oct. 8, 1998

[51] Int. Cl.[6] .................................................. A61F 11/00
[52] U.S. Cl. ........................................ 128/864; 128/867
[58] Field of Search ........................... 128/846, 864–868; 181/135

[56] References Cited

U.S. PATENT DOCUMENTS

| | | | |
|---|---|---|---|
| 2,538,339 | 1/1951 | Thomas | 128/864 |
| 3,800,791 | 4/1974 | Visor | 128/864 |
| 4,219,018 | 8/1980 | Draper | 128/864 |
| 4,936,411 | 6/1990 | Leonard | 128/864 |
| 5,249,309 | 10/1993 | Berg | 128/865 |

*Primary Examiner*—Michael A. Brown
*Attorney, Agent, or Firm*—Charles H. Schwartz

[57] ABSTRACT

An earplug composed of a resilient polymeric material including a first hollow member having a closed end and an open end and with the closed end having a rounded cone shaped configuration. At least one flange member extending from the first hollow member and having a similiar cone shaped configuration as the closed end of the hollow member but larger in diameter and located rearward of the closed end. A plug member for insertion into the open end of the first member and with the plug closing off and sealing the open end of the first member to form an air pocket immediately adjacent the closed end and the flange member.

The plug member serving in combination with the rearward end of the first member as a handle for insertion of the earplug in an ear canal.

23 Claims, 1 Drawing Sheet

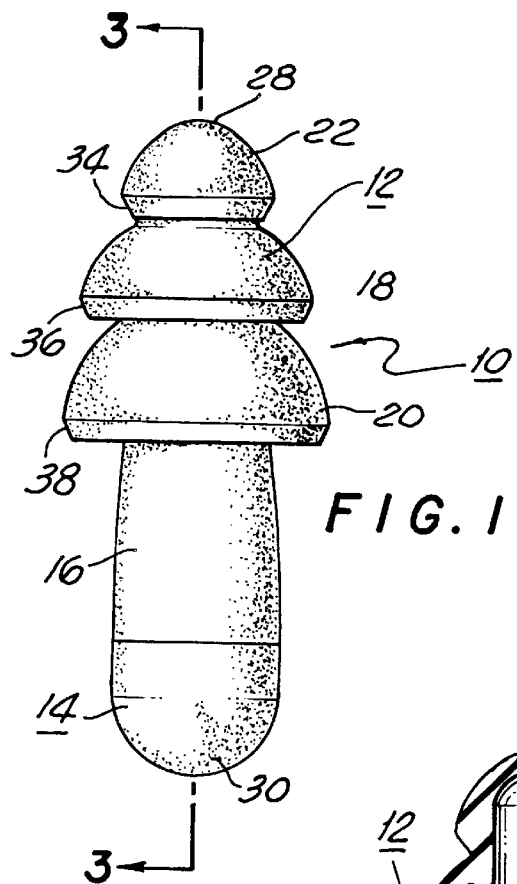
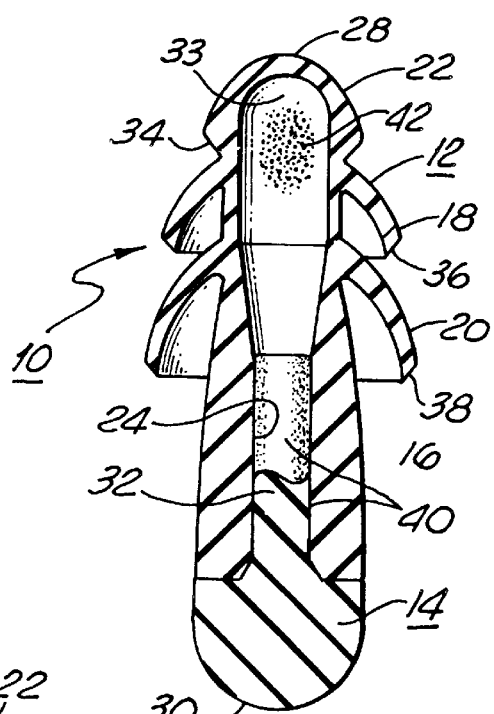
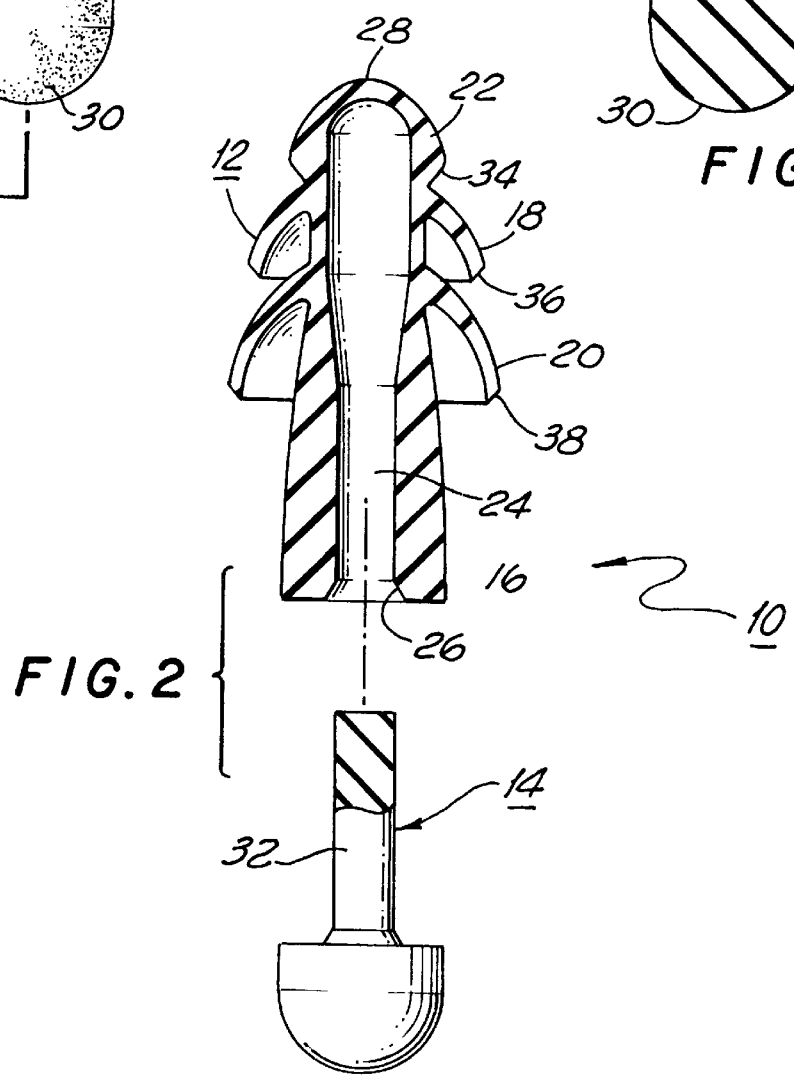
FIG. 1
FIG. 3
FIG. 2

EARPLUG

BACKGROUND OF THE INVENTION

1. Field of the Invention

The present invention relates to an earplug and more specifically is directed to a resilient polymeric earplug having at least one flange and useful as a hearing protector.

2. Prior Art

There is presently on the market a number of earplugs that include a central shaft and extending there from at a nose end at least a single flange. The earplugs are generally composed of a resilient elastomeric material such as synthetic rubber material. The flange element extends outwardly from the nose end of the shaft member and also extends rearwardly from the nose end and is so spaced so as to provide a free annular space between the flange and the shaft. One basic earplug of this type is generally referred to as the V-51R earplug and was developed during the course of World War II in order to provide improved hearing protection to members of the military who were subjected to excessive sound.

In use, the earplug is forcibly inserted into the ear canal, thereby at least partially collapsing the rearwardly extending flange element into the underlying free annular space and conforming the flange element into an acoustic sealing relationship with the walls of the ear canal.

An improved triple flange version of this type of earplug is shown in U.S. Pat. No. 4,867,149 listing Robert N. Falco as the inventor and issued on Sep. 19, 1989. This patent gives further background information on the V-51R earplug and other prior art earplugs of this type. In addition U.S. Pat. No. Des 253, 723 issued on Dec. 18, 1979 listing Howard S Leight as the inventor, also shows a triple flange earplug which is currently on the market.

The prior art earplugs of the type disclosed above typically have a number of problems. For example the earplug shown in U.S. Pat. No. 4,867,149 has a solid shaft member to support the multiple flanges and this type of earplug can create discomfort in a significant proportion of the wearer population. This discomfort would generally be perceived as a sense of excessive pressure being brought to bear on the walls of the ear canal because of the central solid shaft member not flexing to the curvature of the car canal. The central solid shaft member, however, does have the advantage of allowing the earplug to be fully inserted into the ear canal as long as the material used to make the earplug of the U.S. Pat. No. 4,867,149 is of a sufficient hardness to allow for this full insertion.

The product on the market made in accordance with U.S. Pat. No. Des. 253,723 is generally of a softer material than the product made in accordance with the U.S. Pat. No. 4,867,149. In addition the product made in accordance with the U.S. Pat. No. Des. 253,723 is hollow at the tip and therefore is more comfortable in the ear. However, since the product made in accordance with the U.S. Pat. No. Des. 253,723 is of a softer material it is difficult to insert this earplug fully into the ear since the rear end of the earplug does not have sufficient stiffness for the user to fully insert the earplug into the ear.

It would therefore be desirable to have an earplug which is comfortable in the ear, includes at least a single flange member and yet has sufficient rigidity at a rear end portion to enable the user to fully insert the earplug into the ear.

SUMMARY OF THE INVENTION

The present invention provides for an earplug which is comfortable in use and yet has a rear portion of sufficient rigidity so that the earplug can be inserted deeply and easily into the ear. This structure provides for a proper acoustic sealing relationship with the walls of the ear canal and thereby provide for high attenuation of exterior noise to the interior of the ear.

The earplug of the present invention is constructed of front and rear members. One member, located at the rear, forms part of the shaft of the earplug. This rear member is made of a relatively hard polymeric material. The other front member forming the earplug is made of a relatively soft resilient material so as to be comfortable within the interior of the ear. Because of the particular construction of the two members forming the earplug, an air pocket is formed within the earplug at a forward position to provide for a comfortable fit of the earplug within the ear canal. Additionally the forward end of the earplug has a bulbous outer configuration and with at least one flange located rearward of the bulbous end so as to have a tighter sealing relationship with the walls of the earplug.

The earplug of the present invention is thereby formed by a shaft composed of the two members and with at least a single flange member extending from the shaft and a forward end having a bulbous configuration. Both the bulbous end and flange have a rounded cone shape so as to be easily inserted within the ear. An air pocket is formed at the front end of the earplug adjacent the bulbous end and flange so that the air pocket can collapse inwardly as the earplug is received in the ear. This provides for substantial acoustic sealing and yet the earplug is comfortable since the air pocket can conform generally to the size of the ear canal.

BRIEF DESCRIPTION OF THE DRAWING

FIG. 1 is an elevational view of the earplug of the present invention shown to be constructed of two members;

FIG. 2 is an exploded view of the two members of the present invention and with one member partially shown in full and the other member shown in cross-section; and FIG. 3 is a cross-sectional view of the earplug of the present invention taken along lines 3—3 of FIG. 1.

DETAILED DESCRIPTION OF THE PREFERRED EMBODIMENT

As can be seen in FIGS. 1 through 3, an earplug 10 of the present invention is formed of two members 12 and 14 and with member 12 forming a forward member and member, 14 forming a rearward portion. The forward member 12 is to be inserted into the ear canal and with the rearward member 14 facilitating this insertion since it is formed of a stiffer and harder material than member 12.

The member 12 of the earplug 10 is formed of a shaft section 16, a pair of flanges 18 and 20 and a forward bulbous end 22. The flanges 18 and 20 as well as the bulbous end 22 each have a generally rounded cone configuration and extend rearwardly to be received within the ear canal and provide sealing to the walls of the ear canal. As can be seen in FIG. 2, the member 12 has a hollow interior channel 24 which extends the length of the member 12 and has an open end 26 and a closed end 28, conforming to the bulbous end 22.

The member 14 is formed as a plug with a solid back end 30 and extending therefrom is a rod 32 which rod extends through the open end 26 and is received within the channel 24 in the member 12. As shown in FIG. 3, the rod 32 is positioned within the opening 24 to form a rigid handle for insertion of the earplug into the air canal. Also as shown in FIG. 3, an air pocket 33 is formed at the front end of the earplug 10. The air pocket 33 allows the front bulbous end 22 to collapse inward when the ear plug 10 is inserted into the ear.

The air pocket 33 also allows the flanges 18 and 20 to also have the ability to collapse even further so as to make the earplug very comfortable when the bulbous end 22 and the flanges 18 and 20 lie against the walls of the ear canal. It should also be noted that the bulbous end 22 and the flanges 18 and 20 each include a chamfer, designated by reference numbers 34, 36 and 38, which chamfers reduce sharp edges which would tend to be irritating in the ear canal.

The earplug of the present invention can be fabricated by any suitable polymer molding techniques such as by injection molding. It is important that the earplug be constructed of the proper resilient polymer material so as to have the combination of softness at the end of the earplug which is inserted into the ear and hardness at the rearward end to facilitate the insertion.

For example the member 12 and specifically the bulbous end 22 and flanges 18 and 20 should be formulated of material which have a Shore A Durometer hardness value (by the technique of ASTM 2240-81) of between about 10 and 30 and preferably between 15 and 25. The member 14 should be composed of a resilient polymeric material having a higher Shore A Durometer hardness value between 50 and 120 and preferably between 70 and 90. In a preferred embodiment the member 12 can have a Shore A Durometer hardness value of approximately 20 and the member 14 can have a Shore A Durometer hardness value of approximately 85.

It should be noted that the U.S. Pat. No. 4,867,149 also describes using different Shore A Durometer hardnesses value for different portions of the described earplug, but it should be appreciated that it would be difficult to provide for significant differences in hardness within a unitary earplug as opposed to the present invention which provides these differences in two separate members. Also in the present invention when the rod 32 of the member 14 is inserted through the open end 26 into the channel 24 of the member 12, this provides for the rear end of the earplug being stiff and for the formation of the air pocket 33. The front portion of the earplug 10 is thereby more compliant and more comfortable in the ear canal. Again as indicated above other prior art earplugs have had an ear pocket at the forward end but these earplugs have generally been constructed in a different fashion such as shown in U.S. Pat. No. 3,895,627 issued on Jul. 22, 1975 listing Howard S Leight as the inventor or have been composed of a single material as shown in U.S. Pat. No. Des. 253,723 referred to above.

There are many known resilient polymeric materials which may be used to form the earplugs of the present invention. For example, natural rubber, neoprene rubber, SBR rubber (styrene block copolymer compounds), silicone rubber, EPDM rubber, polybutadiene rubber, polyvinylchloride elastomers, polyurethane elastomers, ethylene vinyls, acetate elastomers, elastomers based on acrylic acid precursors and vinyhalide polymers may all be generally suitable materials which can be used to provide the necessary Shore A Durometer values. As preferred materials the present invention contemplates using a polyvinylchloride elastomer with low migration for the member 14 and a SBR rubber for the front and member 12.

As shown in the drawings of the present invention, the member 14 has the rod 32 inserted through the open end 26 into the channel 24 of the member 12 to seal the rod in the channel to form the air pocket 33. Typically friction will maintain the rod 32 within the channel 24 and prevent the rod from being pulled out of the channel 24. However in order to eliminate the possibility of the seal being broken and thereby compromising the air pocket 33, any suitable adhesive material may be coated on the rod 32 and/or be in the channel 24, such as adhesive material 40 shown in FIG. 3. The adhesive material 40 would therefore bond the rod 32 within the channel 24 and seal the rod within the channel and thereby preserve the air pocket 33.

The present invention therefore provides for a two-piece earplug with one rear piece forming a firm handle for the insertion of the other front resilient piece which is inserted into the ear channel. The two-piece earplug has an air pocket adjacent a bulbous front end and flanges to provide for a sealing of the earplug within the ear canal and with a comfortable fitting of the earplug in the ear canal. The present invention therefore provides for a unique combination of materials easily manufactured as separate items, which when combined provides for an earplug having all the desired characteristics which are lacking in the prior art.

Although the present invention has been described with reference to a particular embodiment, it should be appreciated that various adaptations and modifications may be made. For example, ferric powder could be enclosed in the air pocket 33, as shown by powder 42 or as part of the adhesive 40, so that the earplug is magnetically detectable for safety in a food service production line. The invention is only to be limited by the appended claims.

We claim:

1. A two piece earplug composed of resilient polymeric material for insertion into an ear canal, including
    an elongated hollow member having a thin walled closed nose end formed as a bulbous protrusion and an open rear end and with the interior of the elongated hollow member substantially conforming in shape at the nose end to the outer shape of the nose end,
    the elongated hollow member also including at least one hollow rearwardly extending flange element located rearward of the bulbous end,
    both the bulbous end and the at least one flange element having a generally curved cone shape to extend into and conform to the wall of the ear canal, and with the diameter of the curved cone shape of the bulbous end increasing progressively from the closed nose end to a maximum diameter and then decreasing to meet the at least one hollow rearwardly extending flange element,
    a plug member formed with a rod and with the rod sealed within the open rear end on the hollow member to form an air pocket located adjacent the bulbous end and the at least one flange member,
    the hollow member composed of a resilient polymer material having a relatively low Shore A Durometer hardness value and the plug member composed of a resilient polymeric material having a relatively high Shore A Durometer hardness value so that the plug member forms a handle of greater stiffness to enable the hollow member to be more easily inserted into the ear canal and with the relatively low Shore A Durometer hardness value and thin walls of the hollow member and the air pocket providing for greater comfort of the earplug in the ear canal after insertion.

2. The two piece earplug of claim 1 wherein the elongated hollow member includes at least two hollow rearwardly extending flange elements of serially increasing diameters and with the bulbous end having a smaller diameter than any of the flange elements.

3. The two piece earplug of claim 1 wherein the plug member has a larger rear end of substantially the same diameter as the rear end of the hollow member to form a smooth shaft portion rearward of the flange element.

4. The two piece earplug of claim 1 wherein the rod is adhesively attached within the hollow open end of the hollow member.

5. The two piece earplug of claim 1 wherein the hollow member is composed of a resilient polymeric material having a Shore A Durometer hardness value of between 10 and 30 and the plug member is composed of a resilient polymeric material having a Shore A Durometer hardness value of between 50 and 120.

6. The two piece earplug of claim 1 wherein the hollow member has a Shore A Durometer hardness value of between 15 and 25 and the plug member has a Shore A Durometer hardness value of between 80 and 90.

7. The two piece earplug of claim 1 wherein the hollow member has a Shore A hardness value of 21 and the plug member has a Shore A hardness value of 85.

8. The two piece earplug of claim 1 wherein the hollow member is composed of a rubber and the plug member is composed of a vinyl.

9. The two piece earplug of claim 1 wherein the hollow member 1 is composed of a SBR rubber and the plug member is composed of a polyvinylchloride elastomer.

10. The two piece earplug of claim 1 additionally including magnetically detectable material located within the air pocket.

11. An earplug composed of a resilient polymeric material, including a first hollow member having a bulbous closed end and an open end and with the closed end having a thin walled cone shaped configuration substantially uniform in thickness at the closed end, at least one flange member extending from the first hollow member and having a similar cone shaped configuration as the bulbous closed end of the hollow member but larger in maximum diameter and located rearward of the closed end, and with the diameter of the bulbous closed end increasing progressively to a particular diameter less than the maximum diameter of the flange member and then decreasing to meet the flange member, a plug member for insertion into the open end of the first member and with the plug closing off and sealing the open end of the first member to form an air pocket immediately adjacent the thin walled portion of the hollow member forming the closed end and the flange member, and the plug member serving in combination with the rearward end of the first member as a handle for insertion of the earplug in an ear canal.

12. The earplug of claim 11 wherein the first member and the plug member are composed of resilient polymeric material having different hardnesses and wherein the first member is composed of resilient polymeric material significantly softer relative to the hardness of the plug member so that the hardness of the plug member provides for a stiff handle for inserting the earplug into the ear canal.

13. The earplug of claim 11 wherein the elongated hollow member includes at least two rearwardly extending flange members of serially increasing diameters and with the closed end of the hollow member having a smaller diameter then than any of the flange members.

14. The earplug of claim 11 wherein the plug member has a larger rear end of substantially the same diameter as the rear end of the hollow member to form a smooth shaft portion rearward of the flange member.

15. The earplug of claim 11 wherein the plug is adhesively attached within the hollow open end of the hollow member.

16. The earplug of claim 11 wherein the hollow member is composed of a resilient polymeric material having a Shore A Durometer hardness value of between 10 and 30 and the plug member is composed of a resilient polymeric material having a Shore A Durometer hardness value of between 80 and 90.

17. The earplug of claim 11 wherein the hollow member has a Shore A Durometer hardness value of between 15 and 25 and the plug member has a Shore A Durometer hardness value of between 80 and 90.

18. The earplug of claim 11 wherein the hollow member has a Shore A hardness value of 21 and the plug member has a Shore A hardness value of 85.

19. The earplug of claim 11 wherein the hollow member is composed of a rubber and the plug member is composed of a vinyl.

20. The earplug of claim 11 wherein the hollow member 1 is composed of a SBR rubber and the plug member is composed of a polyvinylchloride elastomer.

21. The earplug of claim 11 additionally including magnetically detectable material located within the air pocket.

22. A two piece earplug composed of resilient polymeric material for insertion into an ear canal, including an elongated hollow member having a closed nose end formed as a bulbous protrusion and an open rear end, the elongated hollow member also including at least one hollow rearwardly extending flange element located rearward of the bulbous end, both the bulbous end and at least one flange element having a generally curved cone shape to extend into and conform to the wall of the ear canal and wherein the bulbous end and the at least one flange element has a rear chamfered end so as to reduce sharp edges when the earplug is inserted into the ear canal, a plug member formed with a rod and with the rod positioned within the open rear end on the hollow member to form an air pocket located adjacent the bulbous end and the at least one flange member, the hollow member composed of a resilient polymer material having a relatively low Shore a Durometer hardness value and the plug member composed of a resilient polymeric material having a relatively high Shore A Durometer hardness value so that the plug member forms a handle of greater stiffness to enable the hollow member to be more easily inserted into the ear canal and with the relatively low Shore A Durometer hardness value of the hollow member and the air pocket providing for greater comfort of the earplug in the ear canal after insertion.

23. An earplug composed of a resilient polymeric material, including a first hollow member having a closed end and an open end and with the closed end having a rounded cone shaped configuration, at least one flange member extending from the first hollow member and having a similar cone shaped rounded configuration as the closed end of the hollow member but larger in diameter and located rearward of the closed end and wherein the closed end and the at least one flange member has a rear chamfered end so as to reduce sharp edges when the earplug is inserted into the ear canal, a plug member for insertion into the open end of the first member and with the plug closing off and sealing the open end of the first member to form an air pocket immediately adjacent the closed end and the flange member, and the plug member serving in combination with rearward end of the first member as a handle for insertion of the earplug in an ear canal.

* * * * *